United States Patent
Dubuisson-Brengel et al.

[11] Patent Number: 6,096,890
[45] Date of Patent: Aug. 1, 2000

[54] PROCESS FOR SUBSTITUTED HYDRAZIDES USING CARBOXYLIC ACIDS

[75] Inventors: Catherine Dubuisson-Brengel, Doylestown; Heather Lynnette Rayle, North Wales, both of Pa.

[73] Assignee: Rohm and Haas Company, Phila., Pa.

[21] Appl. No.: 09/383,158

[22] Filed: Aug. 25, 1999

Related U.S. Application Data

[60] Provisional application No. 60/098,059, Aug. 27, 1998.

[51] Int. Cl.[7] ............... C07C 241/04; C07C 243/28; C07C 243/36; C07C 243/38
[52] U.S. Cl. ............... 544/217; 544/218; 546/264; 564/148; 564/149; 564/150; 564/151
[58] Field of Search ............... 544/217, 218; 564/148, 149, 180, 181; 546/264

[56] References Cited

U.S. PATENT DOCUMENTS 4,985,461 1/1991 Hsu et al. ............... 514/615

FOREIGN PATENT DOCUMENTS 0 638 545 A1 2/1995 European Pat. Off. .

OTHER PUBLICATIONS

Kaminski, "2–Chloro–4,6–Disubstituted–1,3,5–Triazines A Novel Group of Condensing Reagents", Tetrahedron Letters, vol. 26 (24), 2901–2904 (1985).

Kaminski, "2–Chloro–4,6–dimethoxy–1,3,5–triazine. A New Coupling Reagent for Peptide Synthesis", Synthesis, 917–920 (1987).

Venkataraman, et al., "Cyanuric Chloride: A Useful Reagent for Converting Carboxylic Acids Into Chlorides, Esters, Amides and Peptides", Tetrahedron Letters, vol. 32, 3037–3040 (1979).

*Primary Examiner*—Mukund J. Shah
*Assistant Examiner*—V Balasubramanian
*Attorney, Agent, or Firm*—Clark R. Carpenter

[57] ABSTRACT

This invention provides a convenient process for the preparation of monoacylhydrazines from carboxylic acids or their salts and hydrazine or substituted hydrazine in the presence of a 1,3,5-triazine substituted with at least one chloro or fluoro. The resulting monoacylhydrazine can further be converted to a diacylhydrazine by effectively either repeating the reaction or through reaction with a carboxylic acid chloride.

14 Claims, No Drawings

PROCESS FOR SUBSTITUTED HYDRAZIDES USING CARBOXYLIC ACIDS

This application claims benefit of priority to U.S. Provisional application Ser. No. 60/098,059 filed on Aug. 27, 1998.

This invention relates to an improved process for the preparation of monoacylhydrazines, some of which are useful intermediates in the synthesis of diacylhydrazine insecticides. In combination with this process for the preparation of monoacylhydrazines, the overall process to the diacylhydrazine insecticides is therefore improved.

Acylhydrazines are typically prepared by coupling a hydrazine with an acid chloride which has been generated from the parent carboxylic acid. This method of preparation is well known and is described in various patents such as U.S. Pat. No. 4,985,461, Jan. 15, 1991. While acid chlorides are highly reactive, they suffer from several disadvantages. The primary disadvantage is economic; though technically simple, conversion of a carboxylic acid to an acid chloride usually adds over $2/lb to the cost of the product. Acid chlorides are corrosive and water-reactive, which presents problems in handling these materials. The environmental impact of this chemistry is also a problem. The hydrogen chloride by-product generated during acid chloride formation and during the process to form the acylhydrazide must be scrubbed and the resulting salts disposed of. The presence of residual chloride in aqueous waste streams is a matter of increasing environmental regulation, so reduction of these by-products in the plant is a matter of some concern. Another concern is that when an acid chloride is reacted with a monosubstituted hydrazine, a mixture of products, because of a lack of regioselectivity, is often produced due to the high reactivity of acid chlorides. These unwanted by-products also add to the cost of producing the desired monoacylhydrazine intermediate and consequently to the cost of the desired diacylhydrazine insecticidal product.

Carboxylic acid anhydrides can be utilized as alternatives to acid chlorides in procedures to form hydrazides as described in EP 0 638 545 A1, published Feb. 15, 1995. However, this procedure is often problematic. If the carboxylic acid is converted to a symmetric anhydride, one equivalent of carboxylic acid is lost as the by-product of the reaction. While expensive acids may be isolated and reconverted to the anhydride, the additional processing required may be costly. If the acid is sufficiently expensive, a mixed anhydride may be prepared from an inexpensive material such as acetic acid. However, it is unlikely that only one of the acid components will couple with the hydrazine, thus resulting in a mixture of hydrazide products being obtained.

N,N'-dicyclohexylcarbodiimide (DCC) and other similar reagents are also used as peptide coupling agents which promotes a variety of acylation reactions between carboxylic acids and nucleophiles. However, these reagents are expensive and form by-products which are difficult to separate from the desired product.

This invention comprises the preparation of hydrazides via a triazine-mediated coupling of carboxylic acids with hydrazines. This invention overcomes the disadvantages of using acid chlorides or acid anhydrides by utilizing carboxylic acids which are more stable and less expensive reagents. Furthermore, this methodology allows the formation of the desired hydrazide with high selectivity. No isomeric or diacylated products were detected.

Although the reaction of 2-chloro-4,6-dialkoxy-1,3,5-triazine, 6-alkoxy-2,4-dichloro-1,3,5-triazine and 2,4,6-trichloro-1,3,5-triazine (cyanuric chloride) with carboxylic acids has been utilized to prepare esters, amides, anhydrides, and peptides as described in Kaminski, *Tetrahedron Lett.* 26, 2901 (1985), Kaminski, *Synthesis* 917 (1987), and Venkataraman et al., *Tetrahedron Lett.* 20, 3037 (1979), the use of these coupling reagents for the formation of hydrazides was neither disclosed nor suggested.

In summary, this invention provides a process comprising the reaction of a carboxylic acid or salt thereof with hydrazine or salt or hydrate thereof, or a substituted hydrazine or salt or hydrate thereof in the presence of a triazine substituted with at least one chloro or fluoro to produce a hydroxytriazine and a monoacylhydrazine or substituted monoacylhydrazine according to the reaction

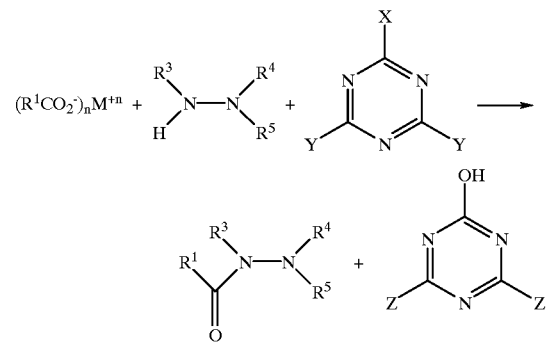

where $R^1$ is a hydrogen atom, alkyl, cycloalkyl, aryl, 5-methyl-6-chromanyl, heteroaryl or aralkyl, $R^2$ is alkyl, aryl or aralkyl, $R^3$, $R^4$ and $R^5$ are each independently selected from a hydrogen atom, alkyl, cycloalkyl, aryl or aralkyl, M is a hydrogen atom or a metal cation, n is 1 or 2, X is fluoro or chloro, each Y is independently selected from fluoro, chloro, $R^2$ and $OR^2$, and each Z is independently selected from hydroxy, $R^2$ and $OR^2$.

In this invention, the term alkyl refers to either a straight chain $(C_1-C_8)$alkyl such as, but not limited to, methyl, ethyl, n-propyl, n-butyl, n-hexyl and n-octyl or a branched chain $(C_3-C_8)$alkyl such as, but not limited to, isopropyl, isobutyl, sec-butyl, tert-butyl, neopentyl, isoamyl, α-methylneopentyl and isooctyl. Cycloalkyl is a cyclo$(C_4-C_8)$alkyl, such as cyclobutyl, cyclopentyl, cyclohexyl and cyclohexyl, all of which may be optionally substituted with alkyl and halo. Halo is fluoro, chloro, bromo or iodo. Alkoxy is a $(C_1-C_4)$ alkyl appended to an oxygen atom and includes, for example, methoxy, ethoxy, n-propoxy, isopropoxy, n-butoxy and tert-butoxy. Alkoxyalkyl is, for example, a $(C_1-C_2)$ alkoxy$(C_1-C_2)$alkyl such as methoxymethyl, ethoxymethyl and ethoxyethyl. Alkythio is a $(C_1-C_4)$alkyl appended to a sulfur atom and includes, for example, methylthio, ethylthio and isopropylthio. Aryl is phenyl, phenyl substituted with from one to three substituents, preferably alkyl, halo, alkoxy and cyano, or naphthyl. Heteroaryl is a 5- or 6-membered aromatic ring containing 1–3 nitrogen atoms, for example, pyridyl, pyrazinyl, pyrimidinyl, triazinoyl, imidazolyl or triazolyl, or a 5-membered aromatic ring containing a sulfur or oxygen atom, for example thienyl or furyl, all of which may be substituted with alkyl or halo. Aralkyl is ar$(C_1-C_4)$ alkyl and includes, for example, benzyl and phenethyl, and aromatic ring portion of which may be further substituted with 1–2 substituents selected from alkyl, halo and cyano. 5-Methyl-6-chromanyl is defined as the moiety having the formula

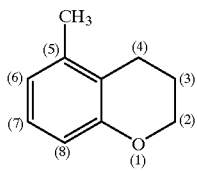

which is attached to another group at position (6).

More specifically, this invention provides a process comprising the reaction of a carboxylic acid or salt thereof with hydrazine or salt or hydrate thereof, or a substituted hydrazine or salt or hydrate thereof in the presence of a triazine substituted with at least one chloro or fluoro to produce a hydroxytriazine and a monoacylhydrazine or substituted monoacylhydrazine according to the reaction

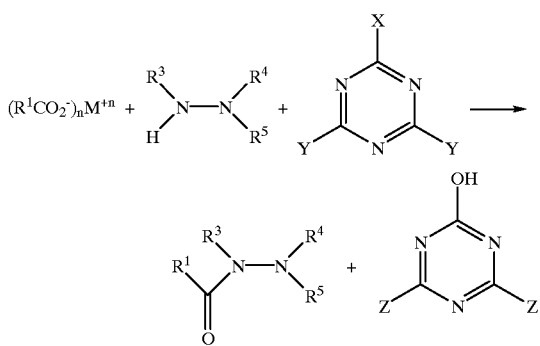

where $R^1$ is a hydrogen atom, $(C_1-C_8)$alkyl, cyclo$(C_5-C_6)$alkyl, naphthyl, phenyl, phenyl substituted with from one to three substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, 5-methyl-6-chromanyl, furyl, thienyl, pyridyl or benzyl, $R^2$ is $(C_1-C_4)$alkyl, phenyl, phenyl substituted with from one to three substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, benzyl or phenethyl, $R^3$, $R^4$ and $R^5$ are each independently selected from a hydrogen atom, $(C_1-C_8)$alkyl, cyclo$(C_5-C_6)$alkyl, phenyl, phenyl substituted with from one to three substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, benzyl or phenethyl, M is a hydrogen atom or a metal cation selected from sodium potassium, lithium, calcium, cesium and barium, n is 1 or 2, X is fluoro or chloro, each Y is independently selected from fluoro, chloro, $R^2$ and $OR^2$, and each Z is independently selected from hydroxy, $R^2$ and $OR^2$.

In a preferred mode of this embodiment, $R^1$ is phenyl, phenyl substituted with from one to two substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, or 5-methyl-6-chromanyl, $R^2$ is $(C_1-C_4)$alkyl or phenyl, $R^3$ and $R^5$ are each independently a hydrogen atom or methyl, $R^4$ is a hydrogen atom, phenyl, straight chain $(C_1-C_4)$ alkyl or a branched chain $(C_3-C_8)$alkyl, M is a hydrogen atom or a metal cation selected from sodium, potassium and lithium, n is 1, X is fluoro or chloro, each Y is independently selected from fluoro, chloro and $OR^2$, and each Z is independently selected from hydroxy and $OR^2$.

In a more preferred mode of this embodiment, $R^1$ is phenyl, phenyl substituted with form one to two substituents independently selected from $(C_1-C_2)$alkyl, $(C_1-C_2)$alkoxy and halo, or 5-methyl-6-chromanyl, $R^2$ is $(C_1-C_2)$alkyl or phenyl, $R^3$ and $R^5$ are each a hydrogen atom, $R^4$ is a branched chain $(C_4-C_6)$alkyl, methyl or phenyl, M is a hydrogen atom or a metal cation selected from sodium, potassium and lithium, n is 1, X is chloro or fluoro, each Y is independently selected from fluoro, chloro and $OR^2$, and each Z is independently selected from hydroxy and $OR^2$.

In an even more preferred mode of this embodiment, $R^1$ is phenyl, 4-ethylphenyl, 4-chlorophenyl, 3-methoxy-2-methylphenyl, 3-ethoxy-2-methylphenyl, 2-ethyl-3-methoxyphenyl, 3-ethoxy-2-ethylphenyl or 5-methyl-6-chromanyl, $R^2$ is methyl, $R^3$ and $R^5$ are each a hydrogen atom, $R^4$ is tert-butyl, M is a hydrogen atom or a metal cation selected from sodium, potassium and lithium, n is 1, X is chloro, each Y is independently selected from chloro and $OR^2$, and each Z is independently selected from hydroxy and $OR^2$.

In these previously described variations of this embodiment, the desired monoacylhydrazine can be purified, if desired, by removal of the hydroxytriazine by-product. These means of purification are known to those with ordinary skill in the art and include removing the hydroxytriazine from the monoacylhydrazine product by various combinations of extractions, washings and/or filtration such as those described in the Examples which follow.

For the purpose of this invention, any salt of a carboxylic acid, i.e., any carboxylate anion, or any carboxylic acid may be utilized. If a carboxylic acid is utilized as the reagent, a base is utilized to prepare the carboxylate anion. The base may be either inorganic, for example, a hydroxide such as sodium or potassium hydroxide, a carbonate such as sodium or potassium carbonate, or a bicarbonate such as sodium bicarbonate, or organic, for example, an amine such as N-methylmorpholine (NMM), triethylamine (TEA) or pyridine, an alkoxide such as potassium tert-butoxide or sodium ethoxide, an alyllithium such as n-butyllithium, or an alkylmagnesium halide (Grignard reagent) such as ethylmagnesium bromide.

Any chlorotriazine or fluorotriazine reagent is acceptable. Examples of suitable triazine reagents include, but are not limited to, 2,4,6-trichloro-1,3,5-triazine (cyanuric chloride), 2,4-dichloro-6-methoxy-1,3,5-triazine, 2-chloro-4,6-dimethoxy-1,3,5-triazine, 2-chloro-4,6-diphenoxy-1,3,5-triazine and 2,4,6-trifluoro-1,3,5-triazine (cyanuric fluoride). When a monochloro or monofluoro 1,3,5-triazine is used, one molar equivalent of carboxylic acid is used per molar equivalent of triazine. If the 1,3,5-triazine is sited with a combination of two chloro and/or fluoro, it is generally most convenient to use two molar equivalents of carboxylic acid per molar equivalent of triazine. If the 1,3,5-triazine is sited with a combination of three chloro and/or fluoro, it is generally convenient to use three molar equivalents of carboxylic acid per molar equivalent of triazine.

Various hydrazines, their hydrate or their corresponding acid addition salts such as the hydrochloride, hydrobromide or sulfate can be used in the process of this invention. Examples of such hydrazines include, but are not limited to, hydrazine, methylhydrazine, N,N'-dimethylhydrazine, phenylhydrazine, isopropylhydrazine, tert-butylhydrazine, neopentylhydrazine, α-methylneopentylhydrazine, isobutylhydrazine, isopentylhydrazine, isooctylhydrazine and their corresponding hydrate or an acid addition salt.

Various polar solvents are employed in the process. Nitriles, such as acetonitrile, or esters, such as n-butyl acetate, are preferred solvents. Non-polar solvents can be utilized, but the isolation of the monoacylhydrazine from the hydroxytriazine by-product is more difficult because of solubility factors.

The reaction temperature under which the reaction is performed will depend upon the solvent chosen and the stability of the hydrazine reactant. Usually a range of from −20° C. to 150° C. is convenient. Preferred are temperatures in the 0° C. to 50° C. range.

Normally the carboxylic acid, solvent and 1,3,5-triazine are added to a suitable reactor, followed by a non-nucleophilic base, such as a tertiary amine, to convert the acid to the carboxylate anion. If sodium hydroxide or a nucleophilic organic base, such as a primary or secondary amine, is used as the base, the addition order is carboxylic acid, solvent and base followed by addition of the 1,3,5-triazine. The mixture is generally held for 15 minutes to 2 hours before addition of the hydrazine and another 30 minutes to 3 hours after the hydrazine addition to complete the reaction.

In a second embodiment of this invention, the monoacylhydrazine formed according to the process of this invention hereinabove described may be reacted with a second carboxylic acid or salt thereof in the presence of a triazine substituted with at least one chloro or fluoro to produce a hydroxytriazine and a diacylhydrazine or substituted diacylhydrazine according to the reaction

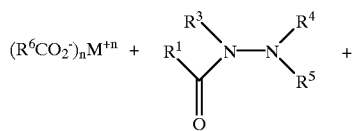

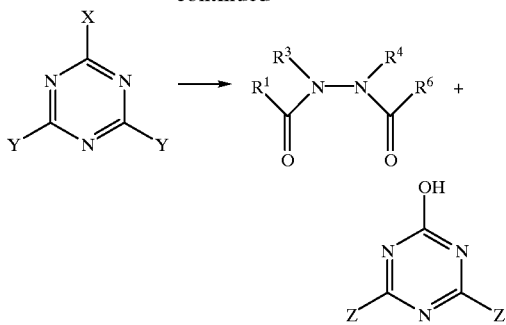

wherein
R$^1$ is a hydrogen atom, alkyl, cycloalkyl, aryl, heteroaryl or aralkyl,
R$^2$ is alkyl, aryl or aralkyl,
R$^3$ and R$^4$ are each independently selected from a hydrogen atom, alkyl, cycloalkyl, aryl or aralkyl,
R$^5$ is a hydrogen atom,
R$^6$ is a hydrogen atom, alkyl, cycloalkyl, aryl, heteroaryl or aralkyl,
M is a hydrogen atom or a metal cation,
n is 1 or 2,
X if fluoro or chloro,
each Y is independently selected from fluoro, chloro, R$^2$ and OR$^2$, and
each Z is independently selected from hydroxy, R$^2$ and OR$^2$.

More specifically, the second embodiment of this invention provides a process comprising the reaction of the monoacylhydrazine formed according to the process of this invention hereinabove described with a second carboxylic acid or salt thereof in the presence of a triazine substituted with at least one chloro or fluoro to produce a hydroxytriazine and a diacylhydrazine or substituted diacylhydrazine according to the reaction

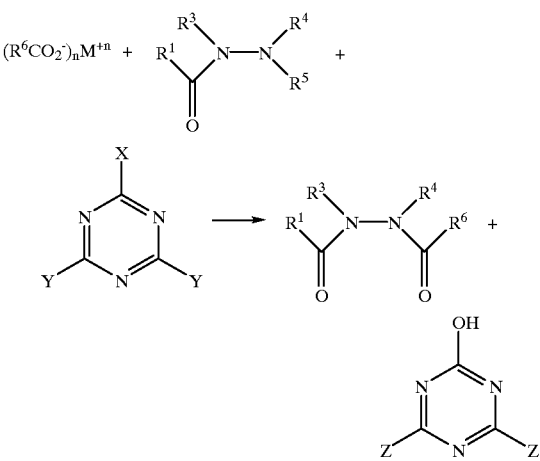

wherein
R$^1$ is a hydrogen atom, (C$_1$–C$_8$)alkyl, cyclo(C$_5$–C$_6$)alkyl, napthyl, phenyl, phenyl substituted with from one to three substituents independently selected from (C$_1$–C$_4$) alkyl, (C$_1$–C$_4$)alkoxy, (C$_1$–C$_2$)alkoxy(C$_1$–C$_2$)alkyl, (C$_1$–C$_4$)alkylthio, halo and cyano, 5-methyl-6-chromanyl, furyl, thienyl, pyridyl or benzyl, $R^2$ is $(C_1-C_4)$alkyl, phenyl, phenyl substituted with from one to three substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, benzyl or phenethyl, $R^3$ and $R^4$ are each independently selected from a hydrogen atom, $(C_1-C_8)$alkyl, cyclo$(C_5-C_6)$alkyl, phenyl, phenyl substituted with from one to three substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, benzyl or phenethyl, $R^5$ is a hydrogen atom, $R^6$ is a hydrogen atom, $(C_1-C_8)$alkyl, cyclo$(C_5-C_6)$alkyl, naphthyl, phenyl, phenyl substituted with from one to three substituents independently selected from $(C_1-C_4)$alkyl, $(C_1-C_4)$alkoxy, $(C_1-C_2)$alkoxy$(C_1-C)$alkyl, $(C_1-C_4)$alkylthio, halo and cyano, furyl, thienyl, pyridyl or benzyl, M is a hydrogen atom or a metal cation selected from sodium, potassium, lithium, calcium, cesium and barium, n is 1 or 2, X if fluoro or chloro, each Y is independently selected from fluoro, chloro, $R^2$ and $OR^2$, and each Z is independently selected from hydroxy, $R^2$ and $OR^2$.

In a preferred mode of this embodiment, $R^1$ is phenyl, phenyl substituted with from one to two substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, or 5-methyl-6-chromanyl, $R^2$ is $(C_1-C_4)$alkyl or phenyl, $R^3$ is a hydrogen atom or methyl, $R^4$ is a hydrogen atom, phenyl, straight chain $(C_1-C_4)$alkyl or a branched chain $(C_3-C_8)$alkyl, $R^5$ is a hydrogen atom, $R^6$ is phenyl or phenyl substituted with from one to two substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, M is a hydrogen atom or a metal cation selected from sodium, potassium and lithium, n is 1, X is fluoro or chloro, each Y is independently selected from fluoro, chloro and $OR^2$, and each Z is independently selected from hydroxy and $OR^2$.

In a more preferred mode of this embodiment, $R^1$ is phenyl, phenyl substituted with from one to two substituents independently selected from $(C_1-C_2)$alkyl, $(C_1-C_2)$alkoxy and halo, or 5-methyl-6-chromanyl, $R^2$ is $(C_1-C_2)$alkyl or phenyl, $R^3$ and $R^5$ are each a hydrogen atom, $R^4$ is a branched chain $(C_4-C_6)$alkyl, methyl or phenyl, $R^6$ is phenyl or phenyl substituted with from one to two substituents independently selected from $(C_1-C_2)$alkyl, $(C_1-C_2)$alkoxy and halo, M is a hydrogen atom or a metal cation selected from sodium, potassium and lithium, n is 1, X is chloro or fluoro, each Y is independently selected from fluoro, chloro and $OR^2$, and each Z is independently selected from hydroxy and $OR^2$.

In an even more preferred mode of this embodiment, $R^1$ is phenyl, 4-ethylphenyl, 4-chlorophenyl, 3-methoxy-2-methylphenyl, 3-ethoxy-2-methylphenyl, 2-ethyl-3-methoxyphenyl, 3-ethoxy-2-ethylphenyl or 5-methyl-6-chromanyl, $R^2$ is methyl, $R^3$ and $R^5$ are each a hydrogen atom, $R^4$ is tert-butyl, $R^6$ is phenyl, 3-methylphenyl, 3,5-dimethylphenyl, 3-chlorophenyl, 3,5-dichlorophenyl or 3-chloro-5-methylphenyl, M is a hydrogen atom or a metal cation selected from sodium, potassium and lithium, n is 1, X is chloro, each Y is independently selected from chloro and $OR^2$, and each Z is independently selected from hydroxy and $OR^2$.

In these previously described variations of this second embodiment, the desired diacylhydrazine can be purified, if desired, by removal of the hydroxytriazine by-product. These means of purification are known to those with ordinary skill in the art and include removing the hydroxytriazine from the diacylhydrazine product by various combinations of extractions, washings and/or filtration.

For the purposes of the second embodiment of this invention, any salt of a carboxylic acid, i.e., any carboxylate anion, or any carboxylic acid may be utilized. If a carboxylic acid is utilized as the reagent, a base is utilized to prepare the carboxylate anion. The base may be either inorganic, for example, a hydroxide such as sodium or potassium hydroxide, a carbonate such as sodium or potassium carbonate, or a bicarbonate such as sodium bicarbonate, or organic, for example, an amine such as N-methylmorpholine (NMM), triethylamine (TEA) or pyridine, an alkoxide such as potassium tert-butoxide or sodium ethoxide, an alkyllithium such as n-butyllithium, or an alkylmagnesium halide (Grignard reagent) such as ethylmagnesium bromide.

Any chlorotriazine or fluorotriazine reagent is acceptable. Examples of suitable triazine reagents include, but are not limited to, 2,4,6-trichloro-1,3,5-triazine (cyanuric chloride), 2,4-dichloro-6-methoxy-1,3,5-triazine, 2-chloro-4,6-dimethoxy-1,3,5-triazine, 2-chloro-4,6-diphenoxy-1,3,5-triazine and 2,4,6-trifluoro-1,3,5-triazine (cyanuric fluoride). When a monochloro or monofluoro 1,3,5-triazine is used, one molar equivalent of carboxylic acid is used per molar equivalent of triazine. If the 1,3,5-triazine is sited with a combination of two chloro and/or fluoro, it is generally most convenient to use two molar equivalents of carboxylic acid per molar equivalent of triazine. If the 1,3,5-triazine is sited with a combination of three chloro and/or fluoro, it is generally convenient to use three molar equivalents of carboxylic acid per molar equivalent of triazine.

Various monoacylhydrazines can be used in the process of the second embodiment of this invention. Examples of such monoacylhydrazines include, but are not limited to, N-benzoyl-N'-tert-butylhydrazine, N-(4-ethylbenzoyl)-N'-tert-butylhydrazine, N-(4-chlorobenzoyl)-N'-tert-butylhydrazine, N-(4-chlorobenzoyl)-N'-phenylhydrazine, N-(4-chlorobenzoyl)-N'-methylhydrazine, N-(3-methoxy-2-methylbenzoyl)-N'-tert-butylhydrazine, N-(3-ethoxy-2-methylbenzoyl)-N'-tert-butylhydrazine, N-(2-ethyl-3- methoxybenzoyl)-N'-tert-butylhydrazine, N-(3-ethoxy-2-ethylbenzoyl)-N'-tert-butylhydrazine and N-(5-methyl-6-chromanoyl)-N'-tert-butylhydrazine.

Various polar solvents are employed in the process. Nitriles, such as acetonitrile, or esters, such as n-butyl acetate, are preferred solvents. Non-polar solvents can be utilized, but the isolation of the diacylhydrazine from the hydroxytriazine by-product is more difficult because of solubility factors.

The reaction temperature under which the reaction is performed will depend upon the solvent chosen and the stability of the hydrazine reactant. Usually a range of from 0° C. to 150° C. is convenient. A convenient temperature is that which is obtained under reflux conditions.

Normally the carboxylic acid, solvent and 1,3,5-triazine are added to a suitable reactor, followed by a non-nucleophilic base, such as tertiary amine, to convert the acid to the carboxylate anion. If sodium hydroxide or a nucleophilic organic base, such as a primary or secondary amine, is used as the base, the addition order is carboxylic acid, solvent and base followed by addition of the 1,3,5-triazine. The mixture is generally held for 15 minutes to 2 hours before addition of the monoacylhydrazine and another 3 to 48 hours after the monoacylhydrazine addition to complete the reaction.

In a third embodiment of this invention, the monoacylhydrazine formed according to the process of this invention hereinabove in the first embodiment described may be reacted with a carboxylic acid chloride to produce a diacylhydrazine or substituted diacylhydrazine according to the reaction

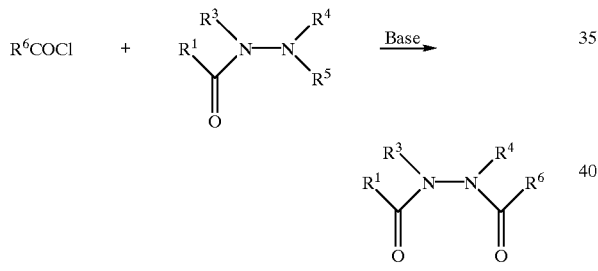

where

R$^1$ is a hydrogen atom, alkyl, cycloalkyl, aryl, heteroaryl or aralkyl,

R$^3$ and R$^4$ are each independently selected from a hydrogen atom, alkyl, cycloalkyl, aryl or aralkyl, R$^5$ is a hydrogen atom, and R$^6$ is a hydrogen atom, alkyl, cycloalkyl, aryl, heteroaryl or aralkyl.

More specifically, the third embodiment of this invention provides a process comprising the reaction of the monoacylhydrazine formed according to the process of this invention hereinabove described in the first embodiment with a carboxylic acid chloride to produce a diacylhydrazine or substituted diacylhydrazine according to the reaction

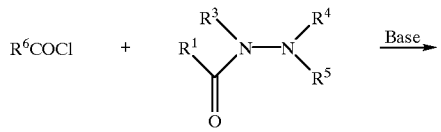

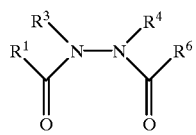

wherein

R$^1$ is a hydrogen atom, (C$_1$–C$_8$)alkyl, cyclo(C$_5$–C$_6$)alkyl, naphthyl, phenyl, phenyl substituted with from one to three substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano, 5-methyl-6-chromanyl, furyl, thienyl, pyridyl or benzyl, R$^3$ and R$^4$ are each independently selected from a hydrogen atom, (C$_1$–C$_8$)alkyl, cyclo(C$_5$–C$_6$)alkyl, phenyl, phenyl substituted with from one to three substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano, benzyl or phenethyl, R$^5$ is a hydrogen atom, and R$^6$ is a hydrogen atom, (C$_1$–C$_8$)alkyl, cyclo(C$_5$–C$_6$)alkyl, naphthyl, phenyl, phenyl substituted with from one to three substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano, furyl, thienyl, pyridyl or benzyl.

In a preferred mode of this embodiment,

R$^1$ is phenyl, phenyl substituted with from one to two substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano, or 5-methyl-6-chromanyl, R$^3$ is a hydrogen atom or methyl, R$^4$ is a hydrogen atom, phenyl, straight chain (C$_1$–C$_4$)alkyl or a branched chain (C$_3$–C$_8$)alkyl, R$^5$ is a hydrogen atom, and R$^6$ is phenyl or phenyl substituted with from one to two substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano.

In a more preferred mode of this embodiment,

R$^1$ is phenyl, phenyl substituted with from one to two substituents independently selected from (C$_1$–C$_2$)alkyl, (C$_1$–C$_2$)alkoxy and halo, or 5-methyl-6-chromanyl, R$^3$ and R$^5$ are each a hydrogen atom, R$^4$ is a branched chain (C$_4$–C$_6$)alkyl, methyl or phenyl, and R$^6$ is phenyl or phenyl substituted with from one to two substituents independently selected from (C$_1$–C$_2$)alkyl, (C$_1$–C$_2$)alkoxy and halo.

In an even more preferred mode of this embodiment,

R$^1$ is phenyl, 4-ethylphenyl, 4-chlorophenyl, 3-methoxy-2-methylphenyl, 3-ethoxy-2-methylphenyl, 2-ethyl-3-methoxyphenyl, 3-ethoxy-2-ethylphenyl or 5-methyl-6-chromanyl, R$^3$ and R$^5$ are each a hydrogen atom, R$^4$ is tert-butyl, and R$^6$ is phenyl, 3-methylphenyl, 3,5-dimethylphenyl, 3-chlorophenyl, 3,5-dichlorophenyl or 3-chloro-5-methylphenyl.

The reaction of the monoacylhydrazine resulting from the first embodiment of this invention with a carboxylic acid chloride is conveniently conducted according to known procedures, for example, as in Step 2 of Process A as described in U.S. Pat. No. 4,985,461, Columns 13–17. Various monoacylhydrazines can be used in the process of the third embodiment of this invention. Examples of such monoacylhydrazines include, but are not limited to, N-benzoyl-N'-tert-butylhydrazine, N-(4-ethylbenzoyl)-N'-tert-butylhydrazine, N-(4-chlorobenzoyl)-N'-tert-butylhydrazine, N-(4-chlorobenzoyl)-N'-phenylhydrazine, N-(4-chlorobenzoyl)-N'-methylhydrazine, N-(3-methoxy-2-methylbenzoyl)-N'-tert-butylhydrazine, N-(3-ethoxy-2-methylbenzoyl)-N'-tert-butylhydrazine, N-(2-ethyl-3-methoxybenzoyl)-N'-tert-butylhydrazine, N-(3-ethoxy-2-ethylbenzoyl)-N'-tert-butylhydrazine and N-(5-methyl-6-chromanoyl)-N'-tert-butylhydrazine.

The following Examples and Tables are meant to guide the practitioner in the use of the invention.

EXAMPLE 1

Formation of N-(p-Chlorobenzoyl)-N'-tert-Butylhydrazine from tert-Butylhydrazine and p-Chlorobenzoic Acid in the Presence of 2-Chloro-4,6-Dimethoxy-1,3,5-Triazine

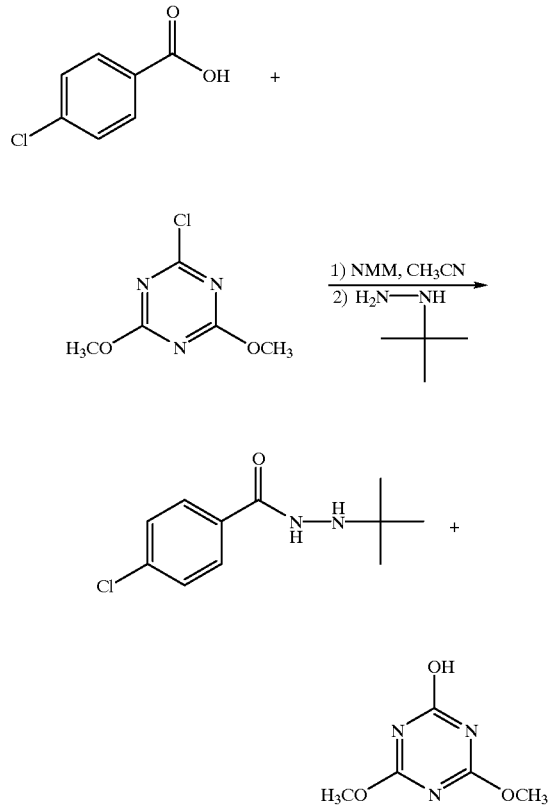

To a stirred and cooled slurry of 4-chlorobenzoic acid (1.00 g, 6.39 mmol) and 2-chloro-4,6-dimethoxy-1,3,5-triazine (1.10 g, 6.26 mmol) in 20 mL of acetonitrile was added N-methylmorpholine (0.65 g, 6.44 mmol) dropwise at such a rate as to keep the temperature at 0° C. A white precipitate formed. After 2 hours (b) of stirring, tert-butyl hydrazine (0.58 g, 6.59 mmol) dissolved in 4 mL of acetonitrile was added. The evolution of the reaction was followed by gas chromatographic (GC) analysis. The reaction was judged to be complete after 1 h at 5° C. The solvent was removed under reduced pressure, and the white residue was dissolved in ethyl acetate and water. The organic layer was washed successively with 10% citric acid solution, saturated sodium bicarbonate solution, and water. The organic layer was dried over sodium sulfate and concentrated in vacuo. The residue was dried under vacuum to yield the desired product (1.22 g, 85%) as a white solid. No isomer or diacylated product was detected by GC analysis.

EXAMPLE 2

Formation of N-(3-Methoxy-2-Methylbenzoyl)-N'-tert-Butylhydrazine from tert-Butylhydrazine and 3-Methoxy-2-Methylbenzoic Acid in the Presence of 2,4,6-Trichloro-1,3,5-Triazine

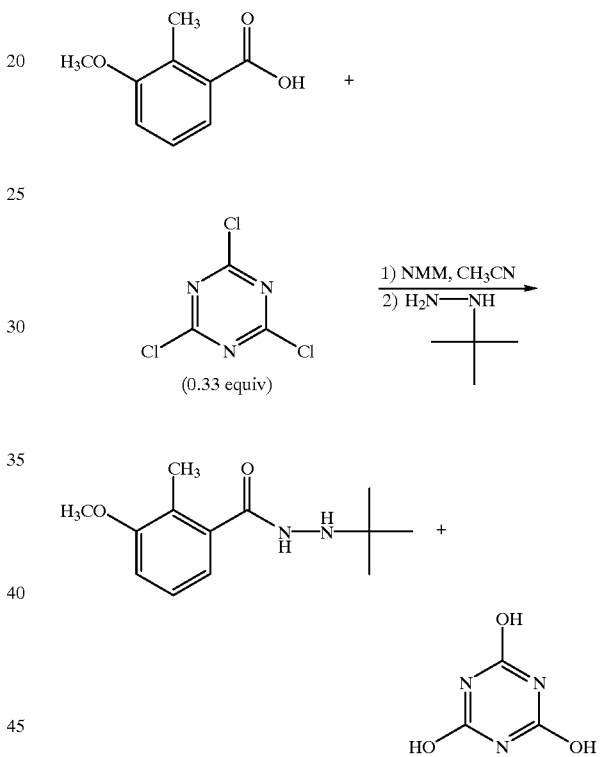

To a stirred slurry of 3-methoxy-2-methylbenzoic acid (1.00 g, 6.02 mmol) and 2,4,6-trichloro-1,3,5-triazine (0.37 g, 2.01 mmol) in 20 mL of acetonitrile was added N-methylmorpholine (0.64 g, 6.34 mmol). A slight exotherm was observed. After 2.5 h of stirring, tert-butyl hydrazine (0.53 g, 6.02 mmol) dissolved in 4 mL of acetonitrile was added. The reaction mixture was stirred at ambient temperature for 2 h and filtered. The solid was washed with a minimal amount of acetonitrile. The filtrates were combined then diluted with sodium hydroxide (1N) and extracted with ethyl acetate. The organic layer was dried over sodium sulfate and concentrated under reduced pressure. Subsequent treatment of the residue with ether and hexanes led to the precipitation of a white solid. The solvent was removed in vacuo to afford 0.92 g (65%) of the desired product.

The results of these examples, and others which were prepared using substantially the same procedures, are summarized in Tables 1–3.

TABLE 1
2-Chloro-4,6-Dimethoxy-1,3-5-Triazine-Mediated Reaction of
Various Benzoic Acids to Form Monoacylhydrazines
| Acid | Base | Solvent | Hydrazine | Product | Yield |
|---|---|---|---|---|---|
| 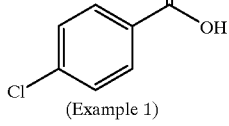 (Example 1) | NMM (N-methylmorpholine) | $CH_3CN$ | 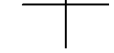 | 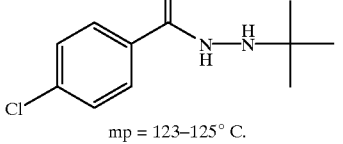 mp = 123–125° C. | 85% |
| 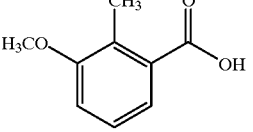 | NMM | $CH_3CN$ |  | 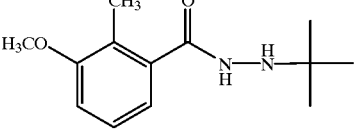 | 77% |
| 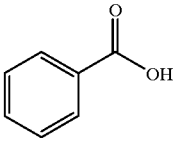 | NMM | $CH_3CN$ | 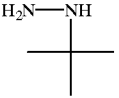 | 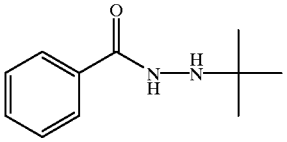 mp = 90–92° C. | 87% |
| 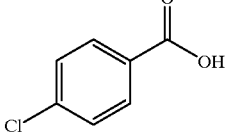 | NMM | $CH_3CN$ |  2 eq. NaOH | 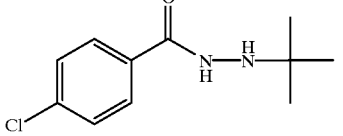 | 80% |
| 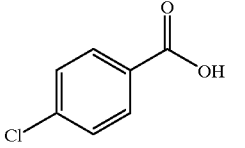 | NMM | Butyl Acetate |  1.5 eq. NaOH | 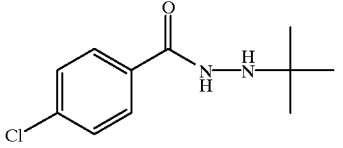 | 64% |
| 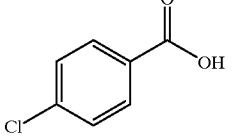 | NMM | $CH_3CN$ | 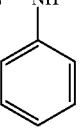 | 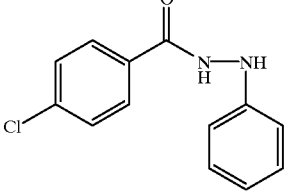 mp = 187–190° C. | 92% |
| 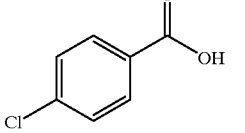 | NMM | $CH_3CN$ |  | 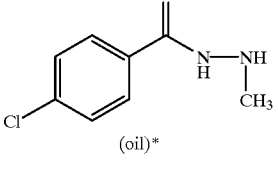 (oil)* | 61% |
| 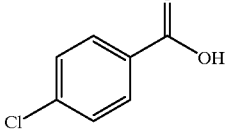 | $Et_3N$ | $CH_3CN$ |  | 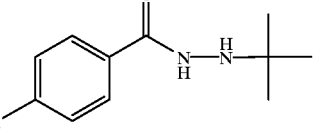 | 66% |

TABLE 1-continued

2-Chloro-4,6-Dimethoxy-1,3-5-Triazine-Mediated Reaction of
Various Benzoic Acids to Form Monoacylhydrazines

| Acid | Base | Solvent | Hydrazine | Product | Yield |
|---|---|---|---|---|---|
|  | NMM | CH$_3$CN | 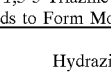 H$_2$N—NH |  mp = 116–119° C. | 82% |

*see NMR data following Table 3.

TABLE 2

2,4-Dichloro-6-Methoxy-1,3-5-Triazine-Mediated Reaction of
p-Chlorobenzoic Acid to Form N-(p-Chlorobenzoyl)-N'-tert-Butylhydrazine

| Acid | Base | Solvent | Hydrazine | Product | Yield |
|---|---|---|---|---|---|
| 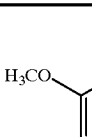 | NMM | CH$_3$CN |  H$_2$N—NH |  mp = 127–129° C. | 71% |

TABLE 3

Cyanuric Chloride-Mediated Reaction of
Various Benzoic Acids to Form Monoacylhydrazines

| Acid | Base | Solvent | Hydrazine | Product | Yield |
|---|---|---|---|---|---|
| 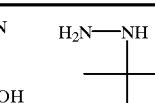<br>(Example 2) | NMM | CH$_3$CN | 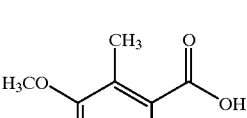 H$_2$N—NH |  mp = 81–83° C. | 65% |
|  | NaOH | CH$_3$CN | 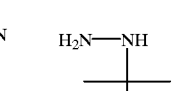 H$_2$N—NH | 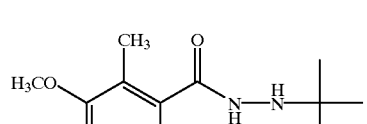 | 50% |
| 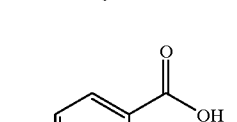 | NMM | CH$_3$CN |  HCl·H$_2$N—NH +<br>1 eq. NMM | 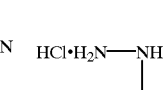 | 50% |

*NMR Data: $^1$H NMR (300 MHz, CDCl$_3$): δ 3.11(s, 3H, CH$_3$), 4.45(br s, 2H, NH), 7.30(s, 4H, ArH).

EXAMPLE 3

Formation of N-(p-Chlorobenzoyl)-N'-Benzoyl)-N'-tert-Butylhydrazine from N-(p-Chlorobenzoyl)-N'-tert-Butylhydrazine and Benzoic Acid in the Presence of 2-Chloro-4,6-Dimethoxy-1,3,5-Triazine

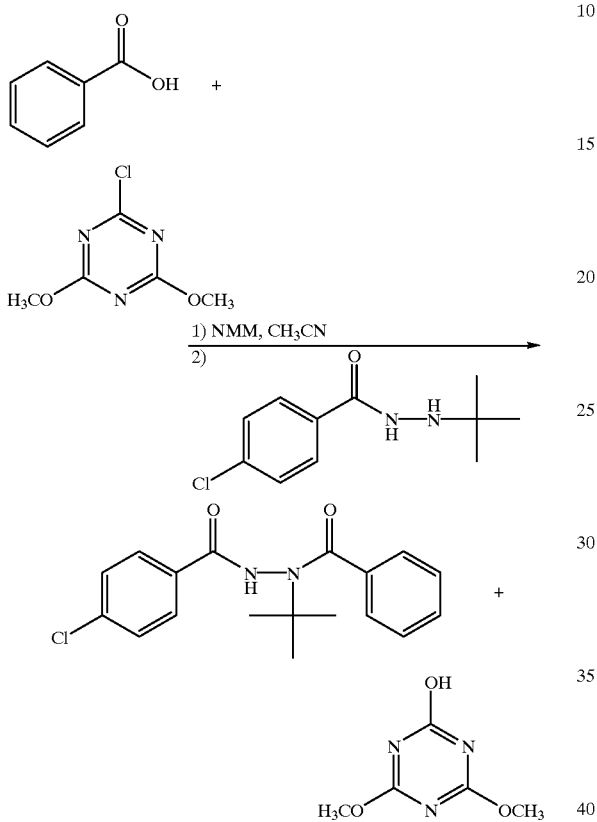

To a stirred slurry of benzoic acid (0.78 g, 6.39 mmol) and 2-chloro-4,6-dimethoxy-1,3,5-triazine (1.10 g, 6.26 mmol) in 20 mL of acetonitrile was added N-methylmorpholine (0.64 g, 6.34 mmol). A white precipitate formed. After 35 minutes of stirring, N-(p-chlorobenzoyl)-N'-tert-butylhydrazine was added. The reaction mixture was stirred at ambient temperature for 19 h and heated at reflux for 6 h. The slurry was then dissolved in dichloromethane and 10% citric acid solution. The organic layer was washed successively with saturated sodium bicarbonate solution and saturated solution of sodium chloride. The organic layer was dried over sodium sulfate and concentrated in vacuo to afford 1.85 g of an orange thick oil. GC analysis of the isolated material showed 26% conversion to the desired product.

We claim:

1. A process comprising the reaction of a carboxylic acid or salt thereof with hydrazine or salt or hydrate thereof, or a substituted hydrazine or salt or hydrate thereof in the presence of a triazine substituted with at least one chloro or fluoro to produce a hydroxytriazine and a monoacylhydrazine or substituted monoacylhydrazine according to the reaction

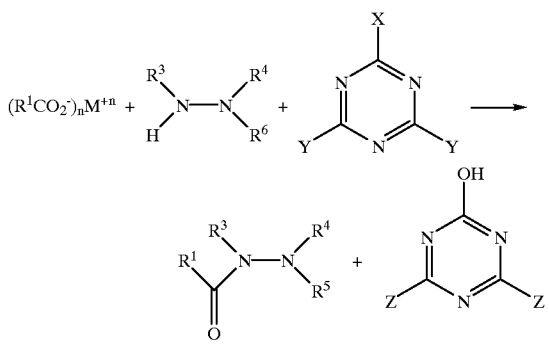

wherein
$R^1$ is a hydrogen atom, $(C_1-C_8)$alkyl, cyclo$(C_5-C_6)$alkyl, naphthyl, phenyl, phenyl substituted with from one to three substituents independently selected from $(C_1-C_4)$ alkyl, $(C_1-C_4)$alkoxy, $(C_1-C_2)$alkoxy$(C_1-C_2)$alkyl, $(C_1-C_4)$alkylthio, halo and cyano, 5-methyl-6-chromanyl, furyl, thienyl, pyridyl or benzyl;

$R^2$ is $(C_1-C_4)$alkyl, phenyl, phenyl substituted with from one to three substituents independently selected from $(C_1-C_4)$alkyl, $(C_1-C_4)$alkoxy, $(C_1-C_2)$alkoxy$(C_1-C_2)$ alkyl, $(C_1-C_4)$alkylthio, halo and cyano, benzyl or phenylethyl;

$R^3$, $R^4$ and $R^5$ are each independently selected from a hydrogen atom, $(C_1-C_8)$alkyl, cyclo$(C_5-C_6)$alkyl, phenyl, phenyl substituted with from one to three substituents independently selected from $(C_1-C_4)$alkyl, $(C_1-C_4)$-alkoxy, $(C_1-C_2)$alkoxy$(C_1-C_2)$alkyl, $(C_1-C_4)$ alkylthio, halo and cyano, benzyl or phenethyl;

M is a hydrogen atom or a metal cation selected from sodium, potassium, lithium, calcium, cesium and barium, n is 1 or 2, X is fluoro or chloro, each Y is independently selected from fluoro, chloro, $R^2$ and $OR^2$, and each Z is independently selected from hydroxy, $R^2$ and $OR^2$.

2. The process of claim 1 wherein
$R^1$ is phenyl, phenyl substituted with from one to two substituents independently selected from $(C_1-C_4)$alkyl, $(C_1-C_4)$alkoxy, $(C_1-C_2)$alkoxy$(C_1-C_2)$alkyl, $(C_1-C_4)$ alkylthio, halo and cyano, or 5-methyl-6-chromanyl, $R^2$ is $(C_1-C_4)$alkyl or phenyl, $R^3$ and $R^5$ are each independently a hydrogen atom or methyl, $R^4$ is a hydrogen atom, phenyl, straight chain $(C_1-C_4)$ alkyl or a branched chain $(C_3-C_8)$alkyl, M is a hydrogen atom or a metal cation selected from sodium, potassium and lithium, n is 1, X is fluoro or chloro, each Y is independently selected from fluoro, chloro and $OR^2$, and each Z is independently selected from hydroxy and $OR^2$.

3. The process of claim 2 wherein
$R^1$ is phenyl, phenyl substituted with form one to two substituents independently selected from $(C_1-C_2)$alkyl, $(C_1-C_2)$alkoxy and halo, or 5-methyl-6-chromanyl, $R^2$ is $(C_1-C_2)$alkyl or phenyl, $R^3$ and $R^5$ are each a hydrogen atom, $R^4$ is a branched chain $(C_4-C_6)$alkyl, methyl or phenyl, M is a hydrogen atom or a metal cation selected from sodium, potassium and lithium, n is 1, X is chloro or fluoro, each Y is independently selected from fluoro, chloro and $OR^2$, and each Z is independently selected from hydroxy and $OR^2$.

4. The process of claim 3 wherein $R^1$ is phenyl, 4-ethylphenyl, 4-chlorophenyl, 3-methoxy-2-methylphenyl, 3-ethoxy-2-methylphenyl, 2-ethyl-3-methoxyphenyl, 3-ethoxy-2-ethylphenyl or 5-methyl-6-chromanyl, $R^2$ is methyl, $R^3$ and $R^5$ are each a hydrogen atom, $R^4$ is tert-butyl, M is a hydrogen atom or a metal cation selected from sodium, potassium and lithium, n is 1, X is chloro, each Y is independently selected from chloro and $OR^2$, and each Z is independently selected from hydroxy and $OR^2$.

5. The process as in any one of the preceding claims further comprising the purification of the monoacylhydrazine by removal of the hydroxytriazine by-product.

6. A process comprising the reaction of a carboxylic acid or salt thereof with hydrazine or salt or hydrate there, or a substituted hydrazine or salt or hydrate thereof in the presence of a triazine substituted with at least one chloro or fluoro to produce a hydroxytriazine and a monoacylhydrazine or substituted monoacylhydrazine according to the reaction

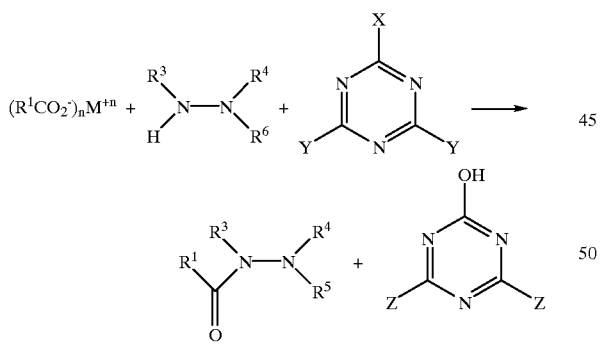

followed by the reaction of the monoacylhydrazine with a second carboxylic acid or salt thereof in the presence of a triazine substituted with at least one chloro or fluoro to produce a hydroxytriazine and a diacylhydrazine or substituted diacylhydrazine according to the reaction

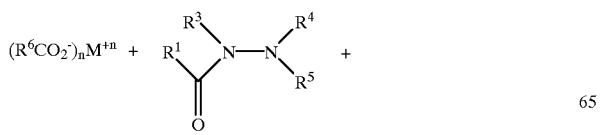

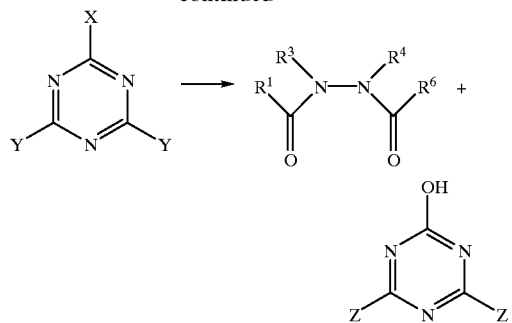

wherein $R^1$ is a hydrogen atom, $(C_1-C_8)$alkyl, cyclo$(C_5-C_6)$alkyl, napthyl, phenyl, phenyl substituted with from one to three substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, 5-methyl-6-chromanyl, furyl, thienyl, pyridyl or benzyl, $R^2$ is $(C_1-C_4)$alkyl, phenyl, phenyl substituted with from one to three substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, benzyl or phenethyl, $R^3$ and $R^4$ are each independently selected from a hydrogen atom, $(C_1-C_8)$alkyl, cyclo$(C_5-C_6)$alkyl, phenyl, phenyl substituted with from one to three substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, benzyl or phenethyl, $R^5$ is a hydrogen atom, $R^6$ is a hydrogen atom, $(C_1-C_8)$alkyl, cyclo$(C_5-C_6)$alkyl, naphthyl, phenyl, phenyl substituted with from one to three substituents independently selected from $(C_1-C_4)$alkyl, $(C_1-C_4)$alkoxy, $(C_1-C_2)$alkoxy$(C_1-C)$alkyl, $(C_1-C_4)$alkylthio, halo and cyano, furyl, thienyl, pyridyl or benzyl, M is a hydrogen atom or a metal cation selected from sodium, potassium, lithium, calcium, cesium and barium, n is 1 or 2, X if fluoro or chloro, each Y is independently selected from fluoro, chloro, $R^2$ and $OR^2$, and each Z is independently selected from hydroxy, $R^2$ and $OR^2$.

7. The process of claim 6 wherein $R^1$ is phenyl, phenyl substituted with from one to two substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, or 5-methyl-6-chromanyl, $R^2$ is $(C_1-C_4)$alkyl or phenyl, $R^3$ is a hydrogen atom or methyl, $R^4$ is a hydrogen atom, phenyl, straight chain $(C_1-C_4)$alkyl or a branched chain $(C_3-C_8)$alkyl, $R^5$ is a hydrogen atom, $R^6$ is phenyl or phenyl substituted with from one to two substituents independently selected from $(C_1-C_4)$alkyl, $(C_1-C_4)$alkoxy, $(C_1-C_2)$alkoxy$(C_1-C_2)$alkyl, $(C_1-C_4)$alkylthio, halo and cyano, M is a hydrogen atom or a metal cation selected from sodium, potassium and lithium, n is 1, X is fluoro or chloro, each Y is independently selected from fluoro, chloro and OR$^2$, and each Z is independently selected from hydroxy and OR$^2$.

8. The process of claim 7 wherein

R$^1$ is phenyl, phenyl substituted with from one to two substituents independently selected from (C$_1$–C$_2$)alkyl, (C$_1$–C$_2$)alkoxy and halo, or 5-methyl-6-chromanyl, R$^2$ is (C$_1$–C$_2$)alkyl or phenyl, R$^3$ and R$^5$ are each a hydrogen atom, R$^4$ is a branched chain (C$_4$–C$_6$)alkyl, methyl or phenyl, R$^6$ is phenyl or phenyl substituted with from one to two substituents independently selected from (C$_1$–C$_2$)alkyl, (C$_1$–C$_2$)alkoxy and halo, M is a hydrogen atom or a metal cation selected from sodium, potassium and lithium, n is 1, X is chloro or fluoro, each Y is independently selected from fluoro, chloro and OR$^2$, and each Z is independently selected from hydroxy and OR$^2$.

9. The process of claim 8 wherein

R$^1$ is phenyl, 4-ethylphenyl, 4-chlorophenyl, 3-methoxy-2-methylphenyl, 3-ethoxy-2-methylphenyl, 2-ethyl-3-methoxyphenyl, 3-ethoxy-2-ethylphenyl or 5-methyl-6-chromanyl, R$^2$ is methyl, R$^3$ and R$^5$ are each a hydrogen atom, R$^4$ is tert-butyl, R$^6$ is phenyl, 3-methylphenyl, 3,5-dimethylphenyl, 3-chlorophenyl, 3,5-dichlorophenyl or 3-chloro-5-methylphenyl, M is a hydrogen atom or a metal cation selected from sodium, potassium and lithium, n is 1, X is chloro, each Y is independently selected from chloro and OR$^2$, and each Z is independently selected from hydroxy and OR$^2$.

10. The process as in claims 6, 7, 8 or 9 further comprising the purification of the diacylhydrazine by removal of the hydroxytriazine by-product.

11. A process comprising the reaction of a carboxylic acid or salt thereof with hydrazine or salt or hydrate thereof, or a substituted hydrazine or salt or hydrate thereof in the presence of a triazine substituted with at least one chloro or fluoro to produce a hydroxytriazine and a monoacylhydrazine or substituted monoacylhydrazine according to the reaction

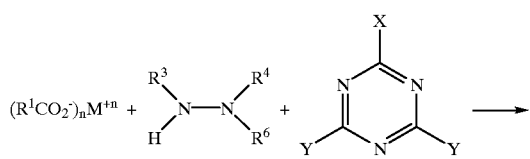

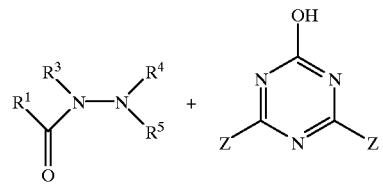

followed by the reaction of the monoacylhydrazine with a carboxylic acid chloride to produce a diacylhydrazine or substituted diacylhydrazine according to the reaction

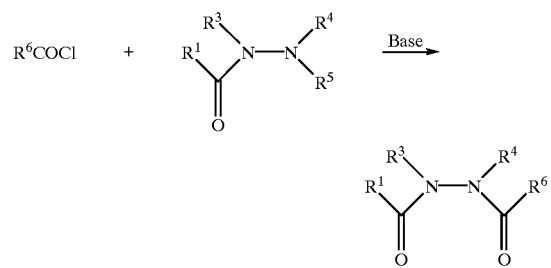

wherein

R$^1$ is a hydrogen atom, (C$_1$–C$_8$)alkyl, cyclo(C$_5$–C$_6$)alkyl, naphthyl, phenyl, phenyl substituted with from one to three substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano, 5-methyl-6-chromanyl, furyl, thienyl, pyridyl or benzyl, R$^3$ and R$^4$ are each independently selected from a hydrogen atom, (C$_1$–C$_8$)alkyl, cyclo(C$_5$–C$_6$)alkyl, phenyl, phenyl substituted with from one to three substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano, benzyl or phenethyl, R$^5$ is a hydrogen atom, and R$^6$ is a hydrogen atom, (C$_1$–C$_8$)alkyl, cyclo(C$_5$–C$_6$)alkyl, naphthyl, phenyl, phenyl substituted with from one to three substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano, furyl, thienyl, pyridyl or benzyl.

12. The process of claim 11 wherein

R$^1$ is phenyl, phenyl substituted with from one to two substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano, or 5-methyl-6-chromanyl, R$^3$ is a hydrogen atom or methyl, R$^4$ is a hydrogen atom, phenyl, straight chain (C$_1$–C$_4$)alkyl or a branched chain (C$_3$–C$_8$)alkyl, R$^5$ is a hydrogen atom, and R$^6$ is phenyl or phenyl substituted with from one to two substituents independently selected from (C$_1$–C$_4$)alkyl, (C$_1$–C$_4$)alkoxy, (C$_1$–C$_2$)alkoxy(C$_1$–C$_2$)alkyl, (C$_1$–C$_4$)alkylthio, halo and cyano.

13. The process of claim 12 wherein

R$^1$ is phenyl, phenyl substituted with from one to two substituents independently selected from (C$_1$–C$_2$)alkyl, (C$_1$–C$_2$)alkoxy and halo, or 5-methyl-6-chromanyl, R$^3$ and R$^5$ are each a hydrogen atom, R$^4$ is a branched chain (C$_4$–C$_6$)alkyl, methyl or phenyl, and $R^6$ is phenyl or phenyl substituted with from one to two substituents independently selected from $(C_1-C_2)$alkyl, $(C_1-C_2)$alkoxy and halo.

14. The process of claim 13 wherein $R^1$ is phenyl, 4-ethylphenyl, 4-chlorophenyl, 3-methoxy-2-methylphenyl, 3-ethoxy-2-methylphenyl, 2-ethyl-3-methoxyphenyl, 3-ethoxy-2-ethylphenyl or 5-methyl-6-chromanyl, $R^3$ and $R^5$ are each a hydrogen atom, $R^4$ is tert-butyl, and $R^6$ is phenyl, 3-methylphenyl, 3,5-dimethylphenyl, 3-chlorophenyl, 3,5-dichlorophenyl or 3-chloro-5-methylphenyl.

* * * * *